(12) United States Patent
Ishizu et al.

(10) Patent No.: US 10,008,048 B2
(45) Date of Patent: Jun. 26, 2018

(54) INFORMATION PROCESSING APPARATUS AND INFORMATION PROCESSING METHOD

(71) Applicant: CANON KABUSHIKI KAISHA, Tokyo (JP)

(72) Inventors: Koichi Ishizu, Kyoto (JP); Takayuki Ueno, Kyoto (JP); Takuya Ishida, Tokyo (JP); Takaaki Endo, Urayasu (JP); Kiyohide Satoh, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days. days.

(21) Appl. No.: 15/678,727

(22) Filed: Aug. 16, 2017

(65) Prior Publication Data
US 2017/0345223 A1 Nov. 30, 2017

Related U.S. Application Data

(63) Continuation of application No. 14/477,324, filed on Sep. 4, 2014, now Pat. No. 9,767,619.

(30) Foreign Application Priority Data

Sep. 11, 2013 (JP) ................................. 2013-188717

(51) Int. Cl.
G09G 5/00 (2006.01)
G06T 19/20 (2011.01)
(Continued)

(52) U.S. Cl.
CPC .............. *G06T 19/20* (2013.01); *A61B 6/461* (2013.01); *A61B 6/502* (2013.01); *A61B 6/5211* (2013.01);
(Continued)

(58) Field of Classification Search
CPC . G06T 19/20; G06T 7/74; G06T 2207/10136; G06T 2207/30068;
(Continued)

(56) References Cited

U.S. PATENT DOCUMENTS 6,311,419 B1 11/2001 Inbar
8,442,286 B2 5/2013 Imamura et al.
(Continued)

FOREIGN PATENT DOCUMENTS

JP 2008-154833 A 7/2008
JP 2009-066074 A 4/2009
(Continued)

OTHER PUBLICATIONS

European Search Report issued in corresponding application No. 1417880.2 dated Jan. 19, 2015.
(Continued)

*Primary Examiner* — Ryan R Yang
(74) *Attorney, Agent, or Firm* — Carter, Deluca, Farrell & Schmidt LLP

(57) ABSTRACT

A tomogram of an object is acquired. A place in a tomogram which corresponds to a portion spaced apart from a reference point in the object by a predetermined distance is specified. A composite image is generated by combining the tomogram with information indicating the specified place. The composite image is output.

35 Claims, 12 Drawing Sheets

(51) Int. Cl.
*A61B 6/00* (2006.01)
*G06T 7/73* (2017.01)
*A61B 8/08* (2006.01)
*A61B 8/14* (2006.01)
*A61B 8/00* (2006.01)

(52) U.S. Cl.
CPC .............. *A61B 8/0825* (2013.01); *A61B 8/14* (2013.01); *A61B 8/4245* (2013.01); *A61B 8/5261* (2013.01); *G06T 7/74* (2017.01); *A61B 8/4263* (2013.01); *A61B 8/463* (2013.01); *G06T 2207/10088* (2013.01); *G06T 2207/10136* (2013.01); *G06T 2207/20221* (2013.01); *G06T 2207/30068* (2013.01)

(58) Field of Classification Search
CPC ....... A61B 6/461; A61B 6/502; A61B 6/5211; A61B 8/0825
USPC .................................................. 345/632, 633
See application file for complete search history.

(56) References Cited

U.S. PATENT DOCUMENTS

| | | | |
|---|---|---|---|
| 9,053,536 B2 | 6/2015 | Imamura et al. | |
| 9,396,576 B2 | 7/2016 | Miyasa et al. | |
| 9,704,294 B2 | 7/2017 | Ishida et al. | |
| 2008/0114244 A1* | 5/2008 | Murashita ................ | A61B 8/14 600/443 |
| 2008/0118111 A1 | 5/2008 | Sirohey et al. | |
| 2009/0069679 A1 | 3/2009 | Hibi | |
| 2010/0220905 A1 | 9/2010 | Katsuhara | |
| 2010/0296623 A1 | 11/2010 | Mielekamp et al. | |
| 2011/0262015 A1* | 10/2011 | Ishikawa ............... | G06K 9/6206 382/128 |
| 2012/0207368 A1* | 8/2012 | Ishikawa ............... | G06T 7/0032 382/128 |
| 2012/0321161 A1 | 12/2012 | Ishikawa et al. | |
| 2013/0066550 A1 | 3/2013 | Takada | |
| 2013/0182901 A1 | 7/2013 | Ishida et al. | |
| 2014/0053066 A1 | 2/2014 | Imamura | |
| 2015/0051489 A1 | 2/2015 | Caluser et al. | |
| 2015/0363080 A1 | 12/2015 | Buelow et al. | |
| 2016/0125584 A1 | 5/2016 | Suzuki et al. | |
| 2016/0180526 A1 | 6/2016 | Satoh et al. | |
| 2016/0180527 A1 | 6/2016 | Endo et al. | |

FOREIGN PATENT DOCUMENTS

| | | |
|---|---|---|
| JP | 2010-500142 A | 1/2010 |
| JP | 2010-227215 A | 10/2010 |
| JP | 2011-123682 A | 6/2011 |
| JP | 2013-000398 A | 1/2013 |
| WO | 2008/020063 A1 | 2/2008 |

OTHER PUBLICATIONS

Japanese office action issued in corresponding application No. 2013188717 dated May 12, 2017.
Japanese Office Action corresponding to Japanese Appln. No. 2017162689 dated Apr. 20, 2018.

* cited by examiner

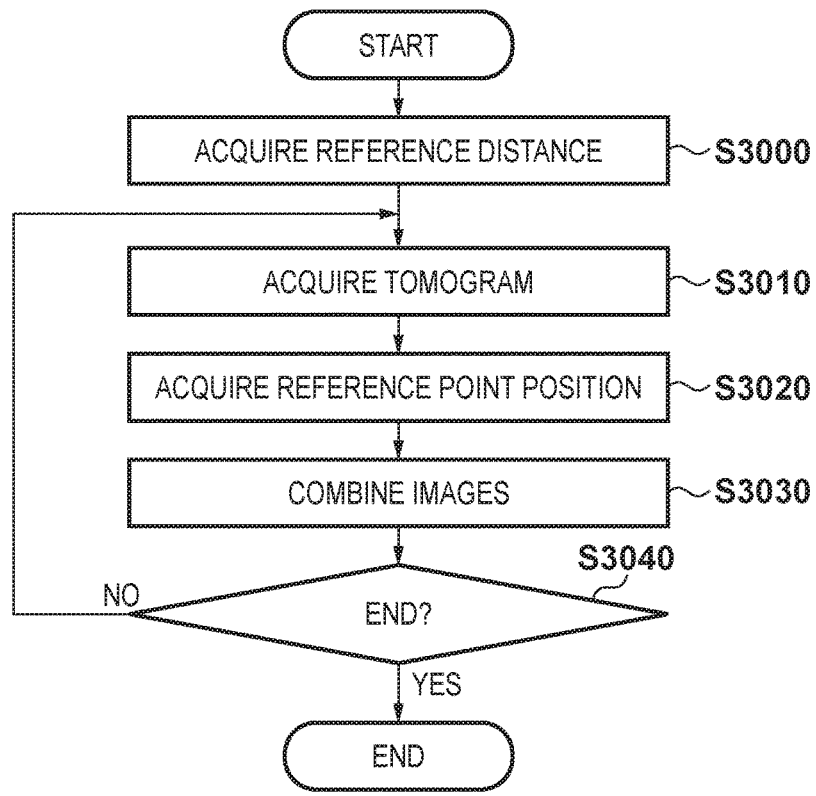
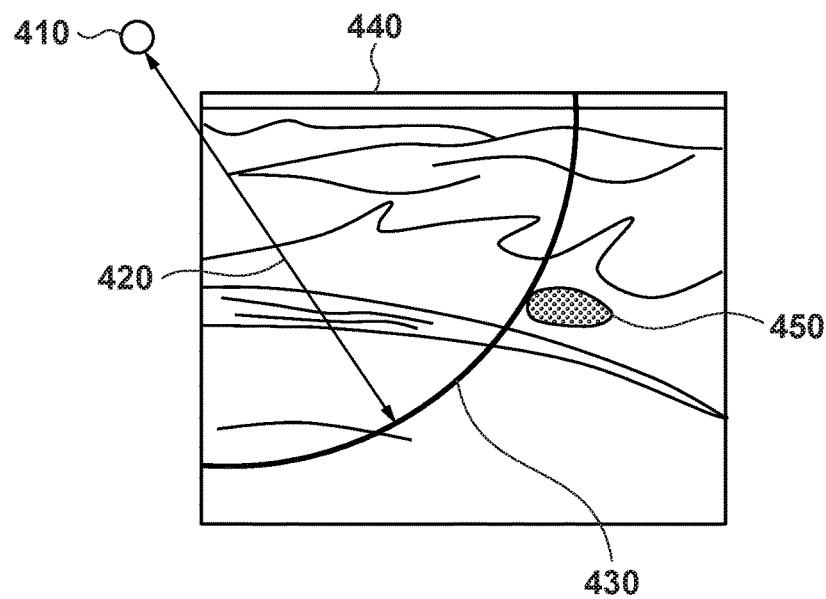

F I G. 11A
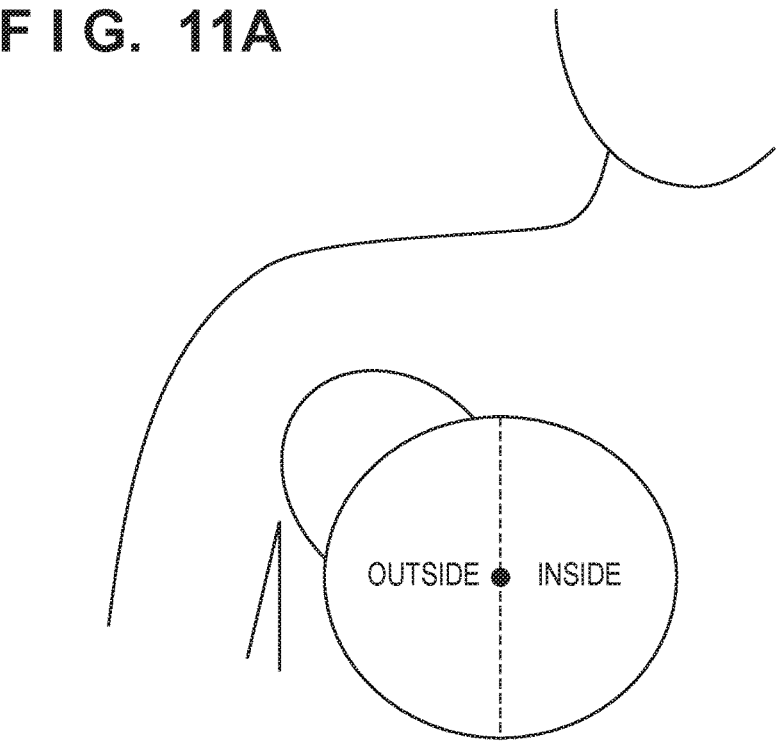
F I G. 11B
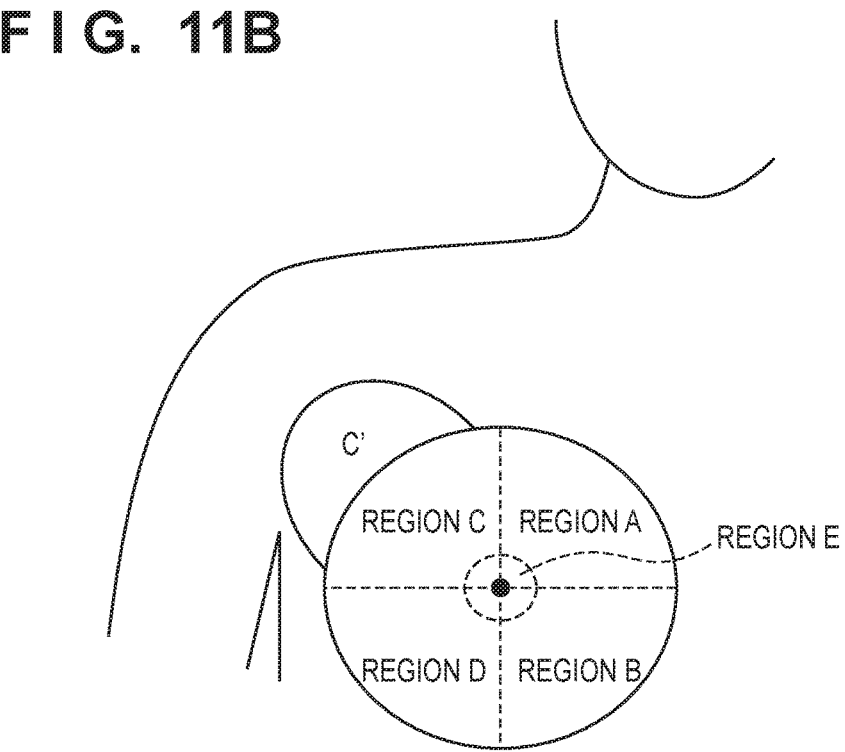

F I G. 15
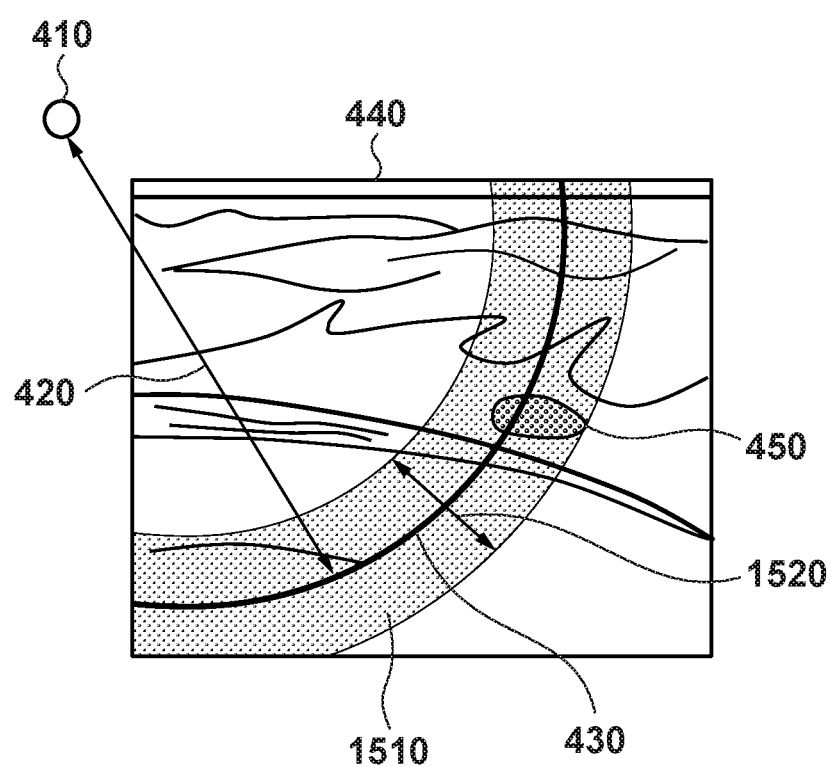

INFORMATION PROCESSING APPARATUS AND INFORMATION PROCESSING METHOD

BACKGROUND OF THE INVENTION

Field of the Invention

The present invention relates to a technique of handling tomograms.

Description of the Related Art

In the medical field, a doctor makes a diagnosis by using the medical images (three-dimensional image data representing three-dimensional information inside an object) captured by a plurality of modalities or medical images captured on different dates. In order to use a plurality of types of medical images for a diagnosis, it is important to associate (identify) a region (a region or lesion of interest) such as a lesion of interest on each medical image. For this reason, the doctor searches for a region (a corresponding region or lesion) corresponding to a lesion of interest pointed out on one medical image from another medical image by using, as clues, similarities in terms of the shape of the lesion, the appearance of a neighboring portion of the lesion, and the like, while seeing the image of the lesion of interest.

In a breast oncology department, after a lesion or the like on an MRI image of the breast imaged in a prone posture is pointed out, a doctor sometimes makes a diagnosis upon searching for (identifying) a corresponding lesion on an ultrasonic tomogram by an ultrasonic examination in a supine posture. However, since the breast as an object is soft and large differences appear between body postures, the position and appearance of a lesion greatly change. This makes it difficult to search for a corresponding lesion. Demands have therefore arisen for a reduction in load by some kind of computer aid.

Patent literature 1 (Japanese Patent Laid-Open No. 2011-123682) discloses a technique of estimating the deformation of the breast from a prone posture to a supine posture. Using this deformation estimation result can estimate the position of a lesion in a supine posture and present the estimated position as support information for the operation of an ultrasonic probe. In addition, patent literature 2 (Japanese Patent Laid-Open No. 2010-227215) discloses a technique of automatically extracting a nipple position from a simple X-ray image of the breast and drawing a region in an image which is included in a predetermined range from the nipple position in the image.

When using the method disclosed in patent literature 1, since it is necessary to perform calculation for a deformation simulation such as a finite element method, the operator (doctor) needs to wait until the end of the calculation. In addition, there are several types of measurement information which the operator should input for the execution of a deformation simulation, but the operator is sometimes not allowed to take time and effort to input such information. In addition, it is not easy to accurately estimate the deformation of the breast itself. In addition, the method disclosed in patent literature 2 allows the operator to know a region within a predetermined range from a feature point of an object. This region is limited to only a slice including the feature point in the image. It is therefore impossible to know the region on an arbitrary slice.

SUMMARY OF THE INVENTION

The present invention has been made in consideration of the above problems, and provides a technique for deriving support information being used when searching for a lesion or the like in an image by only simple calculation, without using many pieces of measurement information, and presenting the support information.

According to the first aspect of the present invention, there is provided an information processing apparatus comprising: a unit configured to acquire a tomogram of an object; and a generation unit configured to specify a place in the tomogram which corresponds to a portion spaced apart from a reference point in the object by a predetermined distance, generate a composite image by combining the tomogram with information indicating the specified place, and output the composite image.

According to the second aspect of the present invention, there is provided an information processing apparatus comprising: a unit configured to acquire a tomogram of an object; a unit configured to acquire a predetermined distance as a distance from a reference point in the object to a lesion in the object; a unit configured to specify a place in the tomogram which corresponds to a portion spaced apart from a position of the reference point by the predetermined distance; and a unit configured to combine information indicating the place with the tomogram and output a composite result.

According to the third aspect of the present invention, there is provided an information processing method performed by an information processing apparatus, comprising: a step of acquiring a tomogram of an object; and a generation step of specifying a place in the tomogram which corresponds to a portion spaced apart from a reference point in the object by a predetermined distance, generating a composite image by combining the tomogram with information indicating the specified place, and outputting the composite image.

According to the fourth aspect of the present invention, there is provided an information processing method performed by an information processing apparatus, comprising: a step of acquiring a tomogram of an object; a step of acquiring a predetermined distance as a distance from a reference point in the object to a lesion in the object; a step of specifying a place in the tomogram which corresponds to a portion spaced apart from a position of the reference point by the predetermined distance; and a step of combining information indicating the place with the tomogram and outputting a composite result.

According to the fifth aspect of the present invention, there is provided an information processing apparatus comprising: a tomogram acquisition unit configured to acquire a tomogram of an object; a reference point position acquisition unit configured to acquire a three-dimensional position of a reference point in the object; a position and orientation acquisition unit configured to acquire a position and orientation of the tomogram; and a display unit configured to superimpose and display, on the tomogram, information concerning a three-dimensional distance from the reference point to each point on the tomogram based on the three-dimensional position of the reference point and the position and orientation of the tomogram.

According to the arrangement of the present invention, it is possible to derive support information when searching for a lesion or the like in an image by only simple calculation, without using many pieces of measurement information, and present the support information.

Further features of the present invention will become apparent from the following description of exemplary embodiments with reference to the attached drawings.

BRIEF DESCRIPTION OF THE DRAWINGS

FIG. 3 is a flowchart showing the processing performed by the computer;

FIG. 4 is a view showing an example of a composite image;

FIGS. 11A and 11B are views for explaining information held in a data server 560;

FIG. 15 is a view for explaining an example of a composite image according to the third embodiment.

DESCRIPTION OF THE EMBODIMENTS

Embodiments of the present invention will be described with reference to the accompanying drawings. Note that each embodiment to be described below will exemplify a case in which the present invention is specifically carried out, and is a specific embodiment having an arrangement described in the scope of claims.

First Embodiment

An information processing system according to this embodiment presents support information for a search to an operator when searching (identifying) for a corresponding region on an ultrasonic tomogram and performing diagnosis by an ultrasonic examination upon pointing out a region of interest such as a lesion on the image acquired by a modality such as MRI. This system presents a place where the possibility of the presence of a corresponding region is high on an ultrasonic tomogram, based on findings that the three-dimensional distance from the nipple to a region of interest such as a lesion (the distance between the nipple and the region of interest) tends to be kept constant, when the breast is an examination target, regardless of a difference in body posture between, for example, a prone posture and a supine posture. In addition, information which allows the operator to grasp the distance from the nipple to each point on an image is displayed on an ultrasonic tomogram to facilitate a search for a corresponding region on the ultrasonic tomogram. The information processing system according to this embodiment will be described below.

Figure 1:
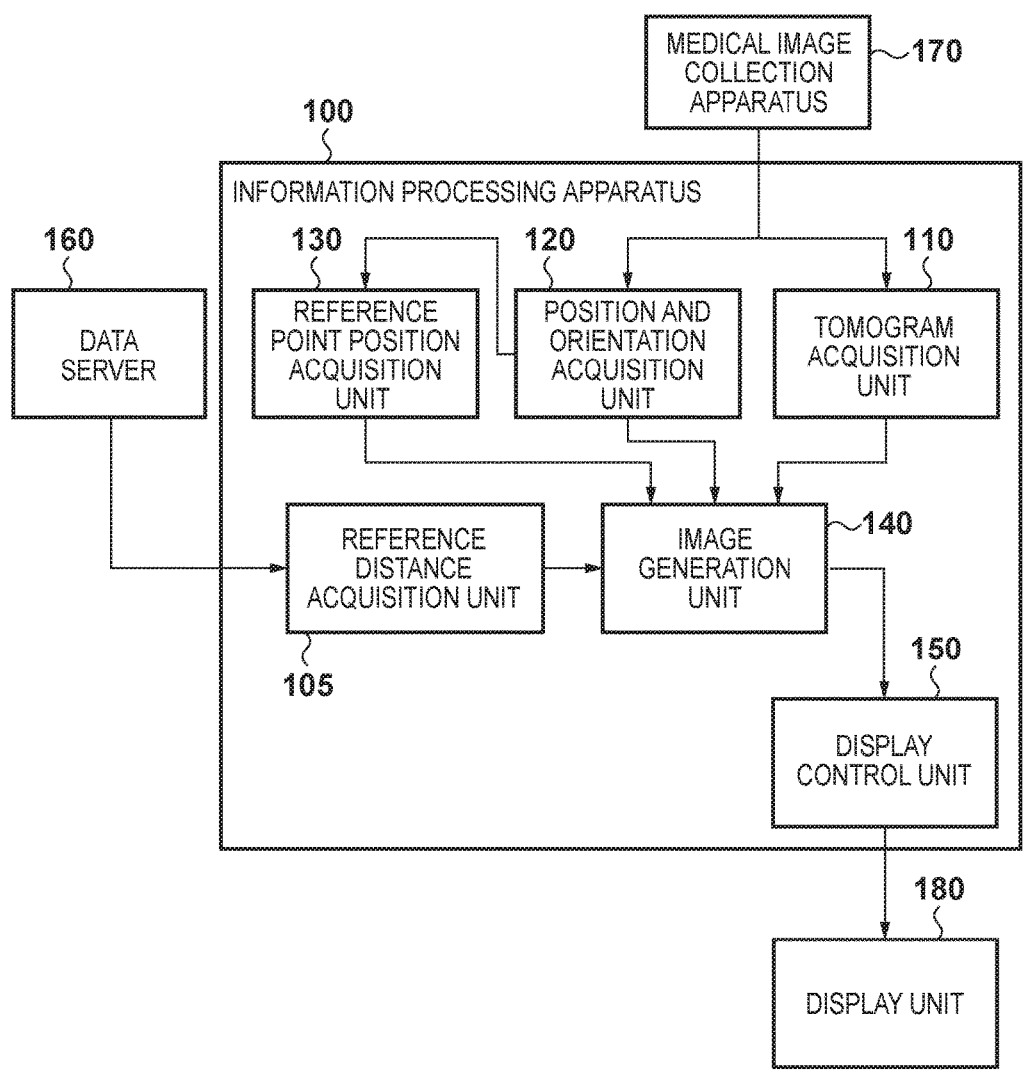
FIG. 1 is a block diagram showing an example of the functional configuration of an information processing system.

An example of the functional configuration of the information processing system according to this embodiment will be described first with reference to the block diagram of FIG. 1. As shown in FIG. 1, the information processing system according to the embodiment includes a data server 160, an information processing apparatus 100, a medical image collection apparatus 170, and a display unit 180.

The data server 160 will be described first. The data server 160 holds information such as a three-dimensional distance from a reference point (the nipple) on an object as an observation target to a region of interest (the distance between the reference point and the region of interest), and outputs the information to the information processing apparatus 100. The distance between the reference point and the region of interest which is held by the data server 160 is a numerical value calculated in advance from other three-dimensional medical images such as MRI images captured by imaging the same object. This value can be acquired by, for example, making the image processing system (not shown) detect the position of the reference point (nipple position) from an MRI image by image processing and calculate the three-dimensional distance between the detected position and the position of a region of interest pointed out on the same image by the operator.

Although FIG. 1 shows the data server 160 as an external apparatus of the information processing apparatus 100, the server may be a device incorporated in the information processing apparatus 100 and may be, for example, a device such as a hard disk incorporated in the information processing apparatus 100.

The medical image collection apparatus 170 will be described next. In this embodiment, the medical image collection apparatus 170 will be described as an ultrasonic image diagnosis apparatus. The medical image collection apparatus 170 captures an ultrasonic tomogram (tomogram) of an object in real time. The medical image collection apparatus 170 sequentially inputs the ultrasonic tomograms of the respective frames captured by the medical image collection apparatus 170 to the information processing apparatus 100 via a tomogram acquisition unit 110. The medical image collection apparatus 170 also includes a sensor system for measuring the position and orientation (three-dimensional position and orientation) of an ultrasonic prove (not shown) in a space in real time. The positions and orientations of the ultrasonic probe which are measured by this sensor system are sequentially input to the information processing apparatus 100 via the position and orientation acquisition unit 120. The sensor system for measuring the position and orientation of the ultrasonic probe may have various arrangements. For example, the sensor system may capture an image of the ultrasonic probe in real time and calculate the position and orientation of the ultrasonic probe from the image by calculation or may measure the position and orientation by a known measurement method using a magnetic sensor, ultrasonic sensor, or optical sensor.

The information processing apparatus 100 will be described next. As the information processing apparatus 100, for example, a general PC (Personal Computer) or dedicated hardware can be used.

A reference distance acquisition unit 105 acquires the distance between a reference point and a region of interest sent from the data server 160 as a reference distance. As described above, the tomogram acquisition unit 110 transfers the ultrasonic tomograms sequentially sent from the medical image collection apparatus 170 to an image generation unit 140 on the subsequent stage. As described above, a position and orientation acquisition unit 120 transfers the positions and orientations sequentially sent from the medical image collection apparatus 170 to the image generation unit 140 on the subsequent stage.

A reference point position acquisition unit 130 acquires the position of a reference point in a space by using the position and orientation of the ultrasonic probe based on an instruction from the operator.

Based on the reference distance, the position of the reference point, and the position and orientation of the ultrasonic prove, the image generation unit 140 calculates a portion (circle) obtained by cutting a sphere centered on the reference point and having the reference distance as a radius along a slice corresponding to an ultrasonic tomogram by performing calculation processing (to be described later). The image generation unit 140 then superimposes (combines) information concerning a portion (arc) of the calculated circle, which is included in the ultrasonic tomogram, on the ultrasonic tomogram, and sends the resultant image to a display control unit 150.

The display control unit 150 sends the composite image sent from the image generation unit 140, that is, the image obtained by superimposing the information concerning the arc on the ultrasonic tomogram, to the display unit 180 to make it display the image.

The display unit 180 is formed from a CRT, liquid crystal display screen, or the like, and displays the processing result obtained by the information processing apparatus 100 in the form of images, characters, or the like. The display unit 180 can display, for example, a composite image (to be described later), GUI (Graphical User Interface), and the like.

The respective functional units constituting the information processing apparatus 100 may all be implemented by hardware but may partly be implemented by software (computer programs). In this case, the control unit of the information processing apparatus 100 executes such software to implement a corresponding function. In addition, one or more of the respective functional units constituting the information processing apparatus 100 may be implemented as independent external devices. Obviously, the respective functional units constituting the information processing apparatus 100 may be implemented by software.

Assume that in this embodiment, all the functional units constituting the information processing apparatus 100 are implemented as software. In this case, a computer having a hardware configuration shown in FIG. 2 can be applied to the information processing apparatus 100.

A CPU 1001 controls the overall operation of a computer by using computer programs and data stored in a RAM 1002 and a ROM 1003, and executes each processing (to be described later) performed by the information processing apparatus 100 to which the computer is applied.

The RAM 1002 has an area for temporarily storing computer programs and data loaded from an external storage apparatus 1007 and a storage medium drive 1008 and data received from an external device via an I/F (Interface) 1009. The RAM 1002 has a work area used when the CPU 1001 executes various types of processing. That is, the RAM 1002 can provide various types of areas, as needed. The ROM 1003 stores set data, boot programs, and the like for this computer.

A keyboard 1004 and a mouse 1005 are used for inputting various types of instructions to the CPU 1001 when the operator operates this computer. Therefore, any devices other than the keyboard 1004 and the mouse 1005 may be used as long as they are devices for inputting various types of instructions to the CPU 1001.

The external storage apparatus 1007 functions as a large-capacity information storage apparatus such as a hard disk drive apparatus. The external storage apparatus 1007 stores an OS (Operating System) and computer programs and data for making the CPU 1001 execute the respective types of processing to be described later as those executed by the information processing apparatus 100 using this computer. The computer programs stored in the external storage apparatus 1007 include computer programs for making the CPU 1001 execute the functions of the functional units (105 to 150) shown in FIG. 1 as functional units in the information processing apparatus 100. The data stored in the external storage apparatus 1007 include those handled as known information in the following description.

The computer programs and data described as those stored in the external storage apparatus 1007 are loaded into the RAM 1002 and become targets to be processed by the CPU 1001, as needed, under the control of the CPU 1001. Note that the information described as that stored in the data server 160 may be stored in the external storage apparatus 1007.

The storage medium drive 1008 reads out a computer program and data stored in a storage medium such as a CD-ROM or DVD-ROM in accordance with an instruction from the CPU 1001, and outputs them to the RAM 1002 or the external storage apparatus 1007. Some of the computer programs and data described as those stored in the external storage apparatus 1007 may be stored in this storage medium.

An I/F 1009 is constituted by a digital input/output port such as an analog video port or IEEE1394, an Ethernet port for outputting information such as a composite image to the outside, and the like. The data server 160, the medical image collection apparatus 170, and the display unit 180 are connected to the I/F 1009. Note that in one form of implementation, some of the functions of the reference distance acquisition unit 105, the tomogram acquisition unit 110, the position and orientation acquisition unit 120, and the reference point position acquisition unit 130 are implemented by the I/F 1009. The respective units described above are connected to each other via a bus 1010.

The processing performed by the computer in FIG. 2 which operates as the information processing apparatus 100 will be described next with reference to FIG. 3 showing a flowchart for the processing. Note that computer programs and data which cause the CPU 1001 to execute processing in accordance with the flowchart of FIG. 3 are stored in the external storage apparatus 1007. The CPU 1001 loads such computer programs and data from the external storage apparatus 1007 into the RAM 1002 and executes processing by using the computer programs and data. This causes the computer in FIG. 2 to execute processing in accordance with the flowchart of FIG. 3.

(Step S3000: Acquisition of Reference Distance)

In step S3000, the CPU 1001 functions as the reference distance acquisition unit 105 to acquire the distance between the reference point and the region of interest sent from the data server 160 as a reference distance. Assume that the data server 160 does not hold the distance between the reference point and the region of interest, and hence it is not possible to obtain the distance between the reference point and the region of interest from the data server 160. In this case, no reference distance is acquired in this step.

(Step S3010: Acquisition of Tomogram)

In step S3010, the CPU 1001 functions as the tomogram acquisition unit 110 to acquire an ultrasonic tomogram from the medical image collection apparatus 170. In addition, in this step, the CPU 1001 functions as the position and orientation acquisition unit 120 to acquire the position and orientation of the ultrasonic probe from the medical image collection apparatus 170 when it has captured the ultrasonic tomogram.

(Step S3020: Acquisition of Reference Point Position)

In step S3020, the CPU 1001 functions as the reference point position acquisition unit 130 to acquire the position of the reference point (nipple position) in a space. In this acquisition processing, when the operator operates the keyboard 1004 (for example, presses a key assigned with a reference point position acquisition command) while keeping a predetermined portion of the ultrasonic probe (for example, the central portion of the prove surface) in contact with the nipple position of the object. That is, when the operator executes the above operation, the CPU 1001 obtains the position of the above predetermined portion from the position and orientation of the ultrasonic probe which is acquired by the position and orientation acquisition unit 120, and acquires the obtained position as the position of a reference point. When obtaining the position of the above predetermined portion from the position and orientation of the ultrasonic probe, the CPU 1001 may use a method of applying a predetermined bias to the position and orientation or a method of performing predetermined matrix transformation.

Note that if a reference point exists inside the body of the object, the operator operates the ultrasonic probe to draw the reference point on an ultrasonic tomogram. Thereafter, the operator points out the coordinates of the reference point on the tomogram to acquire the position of the reference point.

(Step S3030: Image Combining)

In step S3030, the CPU 1001 functions as the image generation unit 140 to generate an image by superimposing information representing a place where the possibility of the presence of a corresponding region is high on an ultrasonic image, and sends the resultant image to the display unit 180.

The processing performed by the image generation unit 140 (CPU 1001) will be described here. First of all, the image generation unit 140 obtains a sphere centered on the position of the reference point obtained in step S3020 and having the reference distance obtained in step S3000 as a radius. The image generation unit 140 obtains a plane in a space containing an ultrasonic tomogram (that is, an ultrasonic slice (imaging slice)) based on the position and orientation of the ultrasonic probe obtained in step S3010, and calculates a circle obtained by cutting the sphere along the plane. Finally, the image generation unit 140 generates a composite image by superimposing a portion (arc), of the calculated circle, which is included in the ultrasonic tomogram, on the ultrasonic tomogram.

FIG. 4 shows an example of a composite image generated by this processing. Referring to FIG. 4, an arc 430, of a circle obtained by cutting a sphere centered on a nipple position 410 as the position of a reference point and having a reference distance 420 as a radius along the plane, which is included in an ultrasonic tomogram is superimposed on an ultrasonic tomogram 440. In this case, the arc 430 is a set of points whose three-dimensional distances from the nipple position 410 coincide with the reference distance obtained in step S3000. If the three-dimensional distance from the nipple to the lesion of object is maintained, since a corresponding region 450 does not exist except for the vicinity of the arc 430, the operator can search for the corresponding region 450 relying on the arc 430.

Note that auxiliary information indicating how much each point on an ultrasonic tomogram differs from the reference distant as a reference (information indicating the relationship between the reference distance and the three-dimensional distance from the reference point to each point on the tomogram) may be presented while being superimposed on this ultrasonic tomogram. For example, several distances are obtained by adding and subtracting predetermined values to and from the reference distance. With regard to the respective obtained distances, spheres are obtained, which are centered on the position of the reference point obtained in step S3020 and have the respective distances as radii. Circles are then obtained in the same manner as described above by cutting the spheres obtained with respect to the respective distances along the above plane, and portions (arcs), of the obtained circles, which are included in the ultrasonic tomogram are superimposed on the ultrasonic tomogram, thereby generating a composite image.

Figure 7:
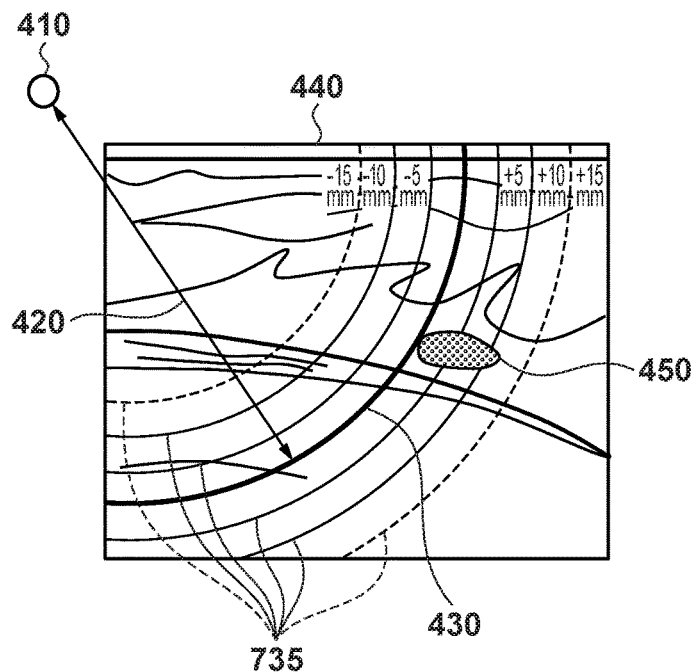
FIG. 7 is a view showing an example of a composite image.

FIG. 7 shows an example of a composite image generated by this processing when a plurality of values (for example, 5 mm, 10 mm, and 15 mm) set at equal intervals are used as predetermined values. Referring to FIG. 7, the arcs obtained from several concentric spheres having, as radii, the values obtained by adding and subtracting the predetermined values to and from the reference distance are superimposed as auxiliary lines 735 on the ultrasonic tomogram 440, together with the arc 430 in FIG. 4. In addition, pieces of character information ("−5 mm", "+10 mm", and the like) indicating how much the respective auxiliary lines differ from the reference distance are superimposed near the auxiliary lines as additional information. Display such a composite image on the display unit 180 allows the operator to know how much each point on the image differs from the distance between the reference point and the region of interest. Note that the line type and color of each auxiliary line may be changed in accordance with the difference from the reference distance. These auxiliary lines may always be drawn or the operator may select to draw or not draw them by operating the keyboard 1004 or the mouse 1005.

Figure 8:
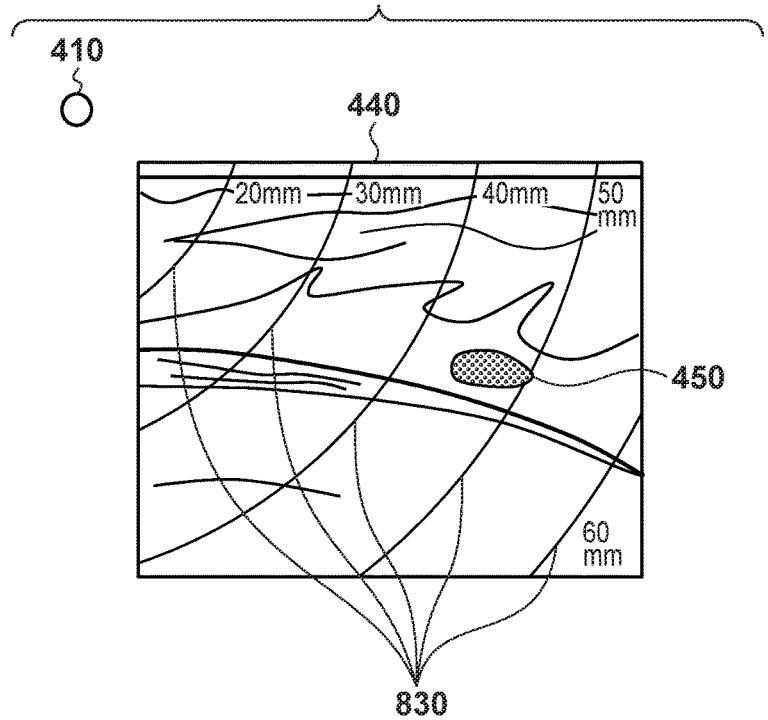
FIG. 8 is a view showing an example of a composite image.

Note that if no reference distance is acquired in step S3000, the image generation unit 140 executes the following processing instead of the above processing. First of all, the image generation unit 140 calculates a plurality of spheres centered on the position of the reference point obtained in step S3020 and having predetermined distances (for example, distances set at intervals of 10 mm from 10 mm to 100 mm) as radii. The image generation unit 140 then calculates circles obtained by cutting these spheres along an ultrasonic slice based on the position and orientation of the ultrasonic probe obtained in step S3010. The image generation unit 140 generates a composite image by superimposing, on the ultrasonic tomogram, portions (arcs), of the plurality of calculated circles, which are included in the ultrasonic tomogram and pieces of information indicating the respective distances. FIG. 8 shows an example of a composite image generated by this processing. Referring to FIG. 8, the arcs obtained from concentric spheres centered on the nipple position 410 and having predetermined distances (20 mm to 60 mm) as radii are superimposed as arcs 830 on the ultrasonic tomogram 440. This display is especially effective when the operator grasps in his/her mind the distance between the reference point and the region of interest. That is, even if the system has not acquired the distance between the reference point and the region of interest, the operator can search for the corresponding region 450 relying on the pieces of information concerning the distances from nipple presented on the ultrasonic tomogram. Even if a reference distance has been acquired in step S3000, the operator may arbitrarily switch between display (display of the distance between the reference point and the region of interest) and main display (display of distances at predetermined equal intervals) in accordance with an instruction issued by the operator via the keyboard 1004 or the mouse 1005. Alternatively, the system may be configured to present a mixture of these pieces of information. Note that if the position of the reference point has not been acquired, the image generation unit 140 outputs the ultrasonic tomogram.

(Step S3040: End Determination)

In step S3040, the CPU 1001 determines whether to end the overall processing. For example, upon detecting that the operator has pressed a predetermined key (end key) of the keyboard 1004, the CPU 1001 determines that the processing is to end.

Upon determining that the processing is to end, the CPU 1001 ends the overall processing. In contrast to this, if the CPU 1001 determines that the processing is not to end, the process returns to step S3010 to execute the processing in step S3010 and the subsequent steps with respect to a newly captured ultrasonic tomogram.

Note that this embodiment has exemplified the case in which the breast is set as an object, and the nipple is set as a reference point. However, the object and reference point to be used are not specifically limited as long as the corresponding object exhibits a tendency that the distance between a region of interest and a reference point is maintained.

As described above, this embodiment allows the operator to easily grasp the three-dimensional distance from the reference point (nipple) to each point on an ultrasonic image. It is possible to present the operator with a place where the possibility of the presence of a corresponding region is high by, especially, indicating a point or neighboring point whose distance from the reference point (nipple) is "distance between reference point and region of interest". According to the embodiment, since indications for a search for a corresponding region in an ultrasonic tomogram are displayed in the ultrasonic tomogram, the operator can limit a search range for the corresponding region. In addition, limiting a search range can reduce the operation load on the operator and reduce the risk of wrong association. In addition, since any calculation such as deformation estimation is not performed, it is possible to support a search for a corresponding region without making the operator wait. Furthermore, since the amount of necessary input information is small, it is possible to support a search for a corresponding region without troubling the operator.

<Modification of First Embodiment>

The first embodiment has exemplified the case in which an ultrasonic image diagnosis apparatus is used as the medical image collection apparatus 170. However, the medical image collection apparatus 170 may be any other modality. If the medical image collection apparatus 170 is CT or MRI, the information processing apparatus 100 acquires a three-dimensional image in advance. In the processing in step S3010, a slice of interest is designated by using a GUI on a known medical image viewer, and a tomogram may be acquired from the three-dimensional image. In addition, the position and orientation of the slice may be acquired. In addition, in the processing in step S3020, the three-dimensional coordinates of a reference point in the three-dimensional image may be acquired by using a GUI like that incorporated in a known medical image viewer.

In addition, the distance between the reference point and the region of interest held by the data server 160 need not be the one obtained from an MRI image. For example, this distance may be the one obtained by obtaining the position of a reference point and the position of a region of interest from an image obtained by another type of modality or obtained in a past ultrasonic examination.

In addition, in the first embodiment, the reference distance acquisition unit 105 has acquired the distance between the reference point and the region of interest from the data server 160. However, a method of acquiring the distance between the reference point and the region of interest is not limited to this. For example, the reference distance acquisition unit 105 may acquire, as a reference distance, the distance input by the operator using a GUI (not shown) and the keyboard 1004 or the mouse 1005. Furthermore, the reference distance acquisition unit 105 may acquire a medical image of an object from the data server 160, and acquire the position of a region of interest and the position of a reference point (nipple position) from the medical image, thereby calculating the distance between the reference point and the region of interest. Alternatively, the reference distance acquisition unit 105 may acquire a medical image of an object and the position of a region of interest from the data server 160, and acquire only the position of a reference point from the medical image, thereby calculating the distance between the reference point and the region of interest. Note that when the reference distance acquisition unit 105 is to acquire the position of a region of interest and the position of a reference point from a medical image, the operator may manually input the positions, or the positions may be automatically detected by image processing.

Second Embodiment

The first embodiment has exemplified the embodiment which can be commonly applied to any targets (is not limited to any specific target) exhibiting a tendency that the distance between a reference point and a region of interest is maintained. The second embodiment will exemplify a case in which the distance between the nipple and a region of interest is acquired from an MRI image in a prone posture, and a target, that is, an organ (breast), a reference point (nipple), and preceding and succeeding postures (prone and supine postures) are specified as when supporting an ultrasonic examination in a supine posture. This embodiment has a feature of acquiring the statistic information of the distances between reference points and regions of interest concerning such specific objects and controlling support information based on the statistic information. The embodiment also has a feature of controlling support information based on statistic information corresponding to the attributes of an object and a region of interest in consideration of the fact that the statistic behaviors of the distances between nipples and regions of interest differ from each other depending on the attributes of objects and regions of interest. In this case, the attributes of objects and regions of interest are those known to make the statistic behaviors of the distances between nipples and regions of interest differ from each other depending on the differences between the attributes. For example, such attributes include the ages of subjects, the breast sizes, and regions to which regions of interest belong in the breasts. An information system according to the embodiment having as its feature to control display by using statistic information will be described concerning only differences from the first embodiment. That is, the remaining portions are the same as in the first embodiment unless specifically mentioned in the following.

An example of the functional configuration of the information processing system according to this embodiment will be described with reference to the block diagram of FIG. 5.

Figure 5:
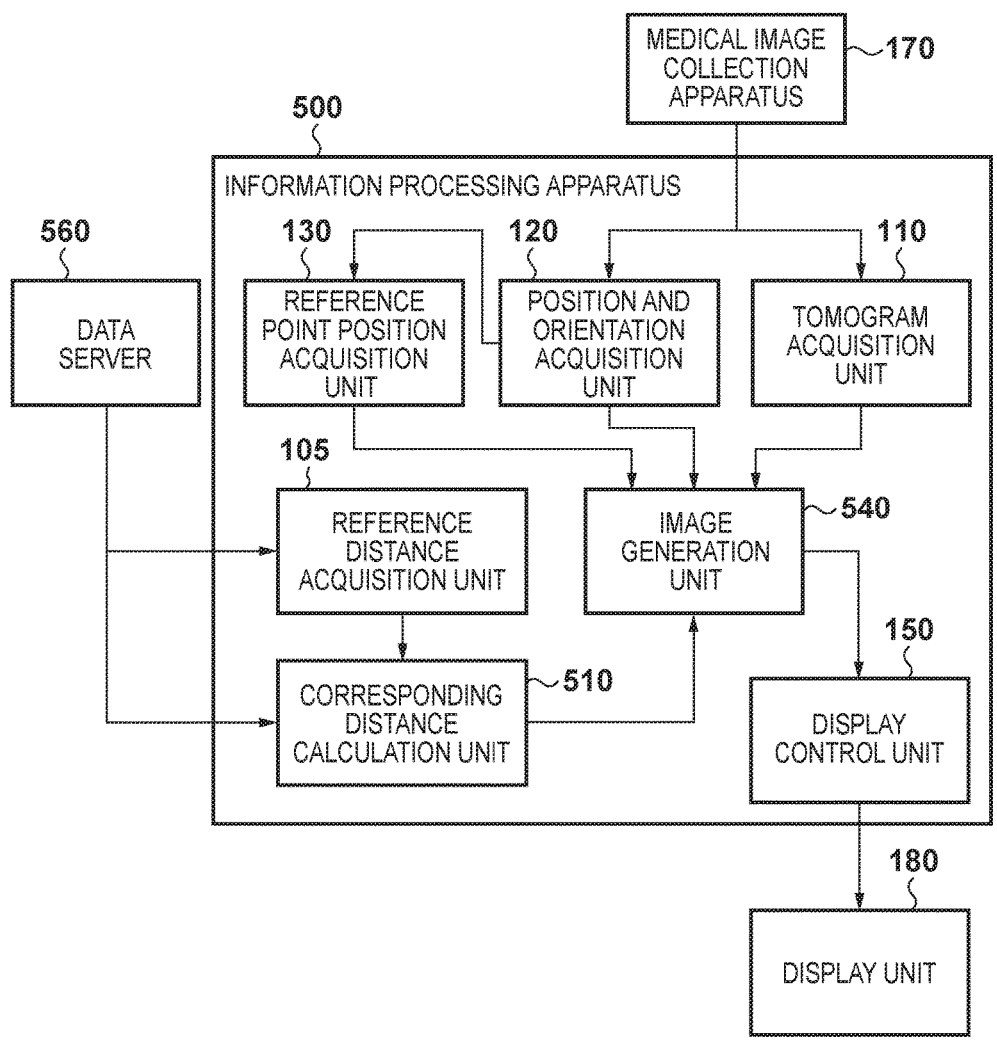
FIG. 5 is a block diagram showing an example of the functional configuration of the information processing system.

Note that the same reference numerals as in FIG. 5 denote the same functional units in FIG. 1, and a description of them will be omitted. As shown in FIG. 5, the information processing system according to this embodiment includes a data server 560, an information processing apparatus 500, a medical image collection apparatus 170, and a display unit 180.

The data server 560 holds, in addition to the distance between the reference point and the region of interest of an object, the three-dimensional image data of the object, based on which the distance between the reference point and the region of interest is acquired. The data server 560 also holds the position (three-dimensional coordinates) of the region of interest in the three-dimensional image data. In addition, the data server 560 holds information representing a specific region in the breast to which a region of interest belongs. For example, the data server 560 holds information representing whether the region of interest belongs to the inside or the outside of the breast, as shown in FIG. 11A. Alternatively, the data server 560 holds information representing whether the region of interest belongs to any of region A (inside upper portion), region B (inside lower portion), region C (outside upper portion), region D (outside lower portion), and region E (areola portion) of the breast, as shown in FIG. 11B. The data server 560 also holds information representing the age and breast size (cup size, the volume of a breast region, or the like) of a subject and the like. The data server 560 outputs the above held data to the information processing apparatus 500.

A corresponding distance calculation unit 510 acquires, from the data server 560, the three-dimensional image data of each subject, the position of a region of interest in the three-dimensional image data, information representing a specific region in the breast to which the region of interest belongs, information of the age and breast size of each subject, and the like. The corresponding distance calculation unit 510 acquires the statistic information of the distances between reference points and regions of interest based on these pieces of information, and calculates an estimated value of the distance between the reference point and a corresponding region (to be referred to as the corresponding distance hereinafter) from the distance between the reference point and the region of interest (reference distance) based on this statistic information. The calculated value of the corresponding distance is output to an image generation unit 540.

Statistic information and a corresponding distance in this embodiment will be described below. If, for example, there is statistic information indicating that when a body posture changes from a prone posture to a supine posture, the distance between the nipple and the region of interest increases by a times on the average, the value obtained by multiplying a reference distance r [mm] by $\alpha$ is set as a corresponding distance r' (the distance at which the corresponding region most likely to exist). Alternatively, if there is statistic information indicating that when a body posture changes from a prone posture to a supine posture, the distance between the nipple and the region of interest is maintained at a standard deviation $\sigma$ [mm], distances respectively represented by r−2$\sigma$, r−$\sigma$, r+$\sigma$, and r+2$\sigma$ are set as corresponding distances (information representing the range of distances at which the corresponding region likely to exist). In addition, assume that if $\alpha$ and $\sigma$ described above have been obtained, r'−2$\sigma$, r'−$\sigma$, r'+$\sigma$, and r'+2$\sigma$ are set as corresponding distances. That is, statistic information in this embodiment represents the above magnification $\alpha$ and standard deviation $\sigma$. In addition, assume that a corresponding distance represents a distance at which a corresponding region is likely to exist after a change in body posture or the range of such distances, which is derived from these pieces of statistic information and reference distances.

The corresponding distance calculation unit 510 manages $\alpha$ and $\sigma$ described above as pieces of statistic information independent of an object, which are calculated by performing statistic processing for many cases (without distinguishing between the cases) by using the measurement values of the distances between the nipples and regions of interest in prone postures and supine postures which have been collected from the cases. The corresponding distance calculation unit 510 manages the statistic information for each of regions (inside and outside regions or regions A to E), which is calculated by performing statistic processing for many cases for each region upon classifying the cases according to the regions to which lesions belong. Likewise, the corresponding distance calculation unit 510 manages statistic information for each segment based on each criterion, which is calculated by performing statistic processing for many cases upon segmenting the ages and breast sizes of subjects, the distances between nipples and regions of interest, the distances between body surfaces and regions of interest, mammary gland densities, and the like into predetermined segments and classifying the many cases according to the respective criteria. Note that it is not essential to use the values obtained by actually performing statistic processing for many cases as statistic information, and it is possible to use the values manually set (by the apparatus designer or the like).

Note that the manner of managing statistic information is not limited to the method of holding statistic information for each segment, which has undergone statistic processing, and another method may be used. For example, a function of x approximating statistic information may be held, with an input parameter x being a combination of at least one or more of the age of each subject, the breast size, the distance between the nipple and the region of interest, the distance between the body surface and the region of interest, the mammary gland density, and the like. That is, statistic information may be managed in the form of function f_$\alpha$(x) which inputs x and outputs $\alpha$ or function f_$\sigma$(x) which inputs x and outputs $\sigma$.

Based on the corresponding distance calculated by the corresponding distance calculation unit 510, the reference point position, and the position and orientation of the ultrasonic probe, the image generation unit 540 calculates a circle obtained by cutting a sphere centered on the reference point and having the corresponding distance as a radius along a slice. The image generation unit 540 generates a composite image by superimposing, on the ultrasonic tomogram, information concerning a portion (arc), of the calculated circle, which is included in the ultrasonic tomogram, and sends the image to a display control unit 150. That is, the composite image is generated in this embodiment in the same manner as in the first embodiment except that a corresponding distance is used instead of a reference distance.

Figure 2:
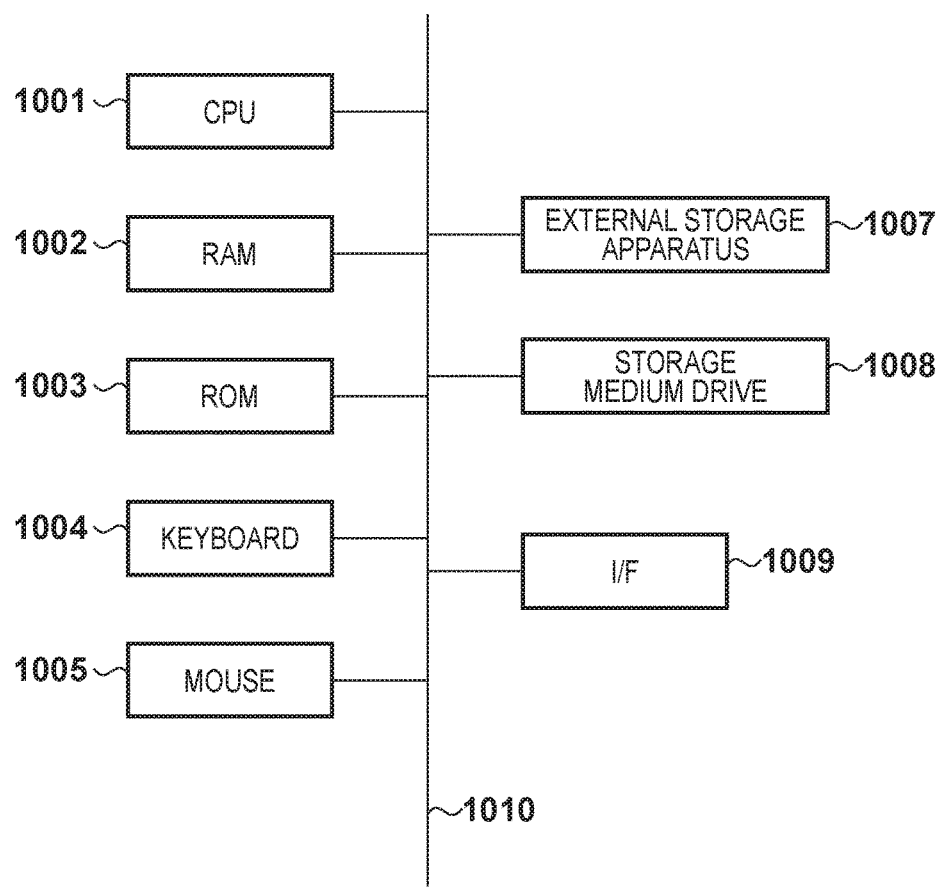
FIG. 2 is a block diagram showing an example of the hardware configuration of a computer.

Note that when the respective functional units in the information processing apparatus 500 shown in FIG. 5 are implemented by computer programs, the computer in FIG. 2 can be applied to the information processing apparatus 500 as in the first embodiment. That is, when the respective functional units in the information processing apparatus 500 are implemented by computer programs, a CPU 1001 executes the computer programs to make the computer function as the information processing apparatus 500.

Figure 6:
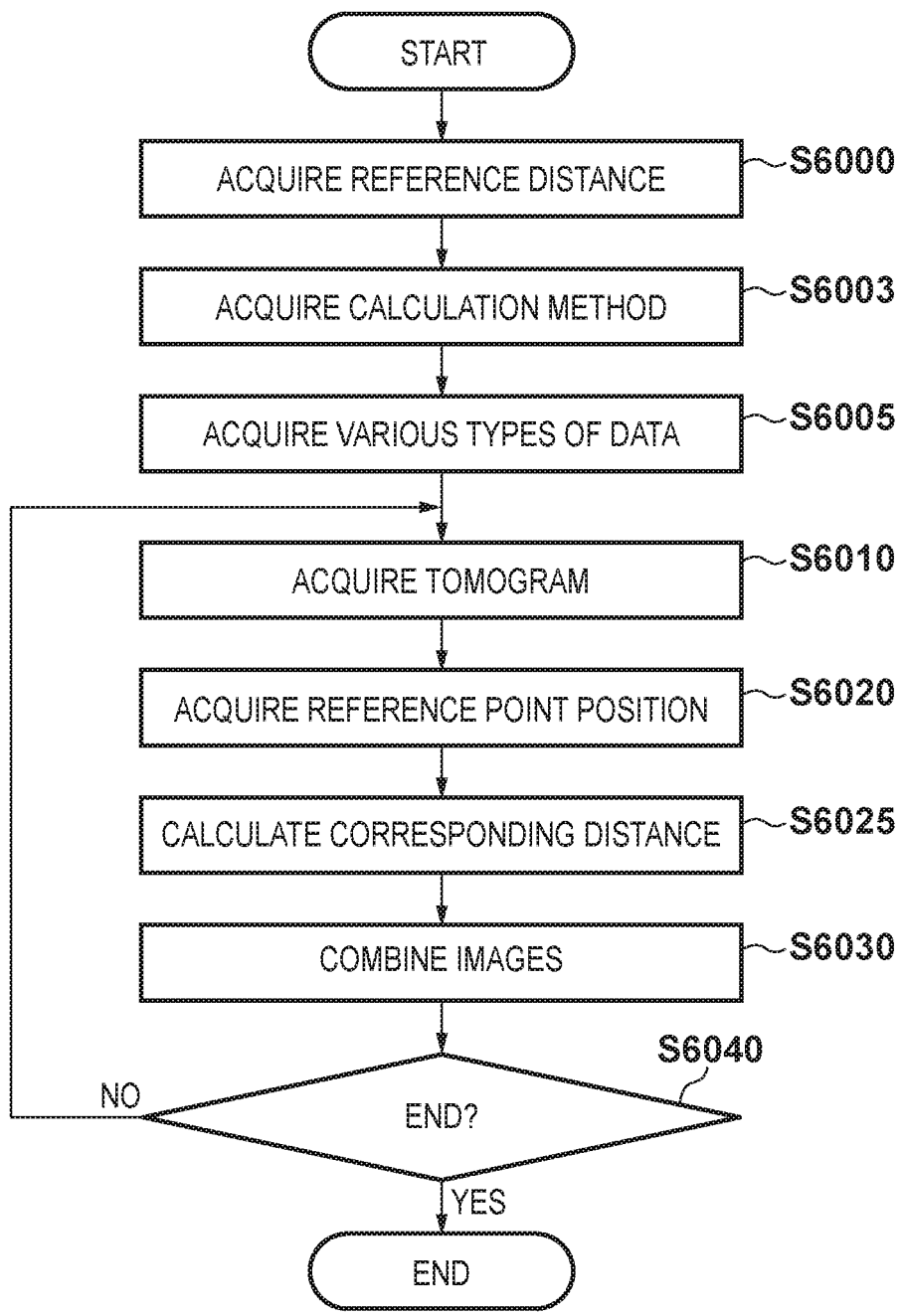
FIG. 6 is a flowchart showing the processing performed by the computer.

The processing performed by the computer in FIG. 2 which operates as the information processing apparatus 500 will be described with reference to FIG. 6 showing a flowchart for the processing. Note that an external storage apparatus 1007 stores computer programs and data which make the CPU 1001 execute the processing based on the flowchart of FIG. 6. The CPU 1001 loads the computer programs and data from the external storage apparatus 1007 into a RAM 1002, and executes processing by using the computer programs and data. This makes the computer in FIG. 2 execute the processing based on the flowchart of FIG. 6.

Steps S6000, S6010, S6020, and S6040 in FIG. 6 are the same as steps S3000, S3010, S3020, and S3040 in the flowchart shown in FIG. 3, and hence a description of these steps will be omitted.

(Step S6003: Acquisition of Calculation Method)

In step S6003, the CPU 1001 acquires the corresponding distance calculation method input by the operator by, for example, pressing a predetermined key on the keyboard 1004. In this embodiment, the operator selects one of the following calculation methods:
1. calculation based on statistic information independent of an object;
2. calculation based on a region to which a region of interest belongs;
3. calculation based on the age and breast size of a subject;
4. calculation based on the distance from a nipple to a region of interest (distance between the nipple and the region of interest);
5. calculation based on the distance from a body surface to a region of interest (distance between the body surface and the region of interest); and
6. calculation based on the mammary gland density of an object.

For example, a GUI displaying these six options in a selectable manner is displayed on a display unit 180. When the operator inputs an instruction to select one of these six options by using the keyboard 1004 or a mouse 1005, the CPU 1001 may detect the selected option as a calculation method to be used subsequently.

Obviously, the method of designating a calculation method is not limited to this method. A calculation method may be determined in advance or determined in accordance with examination contents or the department to which the computer belongs. In addition, options (calculation methods) are not limited to the above six methods.

(Step S6005: Acquisition of Various Types of Data)

In step S6005, the CPU 1001 functions as a corresponding distance calculation unit 510. This makes the CPU 1001 acquire, from the data server 560, a reference distance, the three-dimensional image data of an object, the position of a region of interest in the three-dimensional image data, information indicating a specific region in the breast to which the region of interest belongs, the age and breast size information of the subject, and the like.

(Step S6025: Calculation of Corresponding Distance)

In step S6025, the CPU 1001 functions as the corresponding distance calculation unit 510 to calculate the above corresponding distance based on the data acquired in step S6005. The CPU 1001 executes this processing by obtaining the magnification $\alpha$ and the standard deviation $\sigma$ as statistic information and obtaining the representative value r' of a corresponding distances and its range of r'$-2\sigma$, r'$-\sigma$, r'$+\sigma$, and r'$+2\sigma$ from the reference distance r based on the obtained values.

If method 1 (calculation based on statistic information independent of an object) is selected in step S6003, the CPU 1001 selects the pieces of statistic information $\alpha$ and $\sigma$ independent of an object as statistic information to be used subsequently.

Figure 12A:
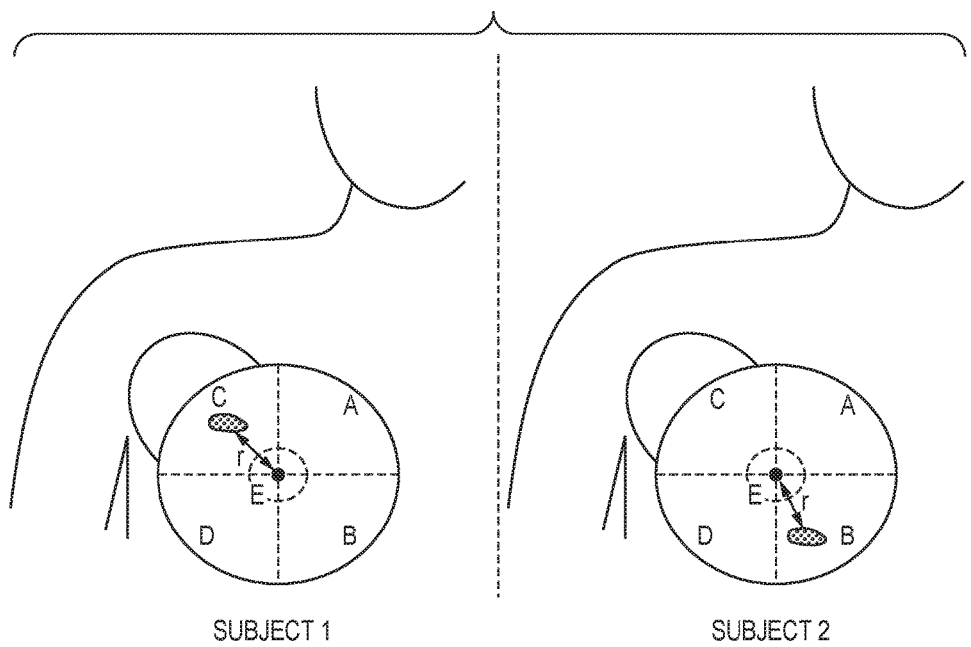
FIGS. 12A and 12B are views for explaining statistic information.

If method 2 in step S6003 (calculation based on a region to which a region of interest belongs), the CPU 1001 selects, as statistic information to be used subsequently, the values of $\alpha$ and $\sigma$ corresponding to a region (one of inside and outside regions or one of regions A to E) to which the region of interest acquired in step S6005 belongs. Assume that a region of interest in subject 1 exists in region C, and a region of interest in subject 2 exists in region B, as shown in FIG. 12A. In this case, in processing in this step, the CPU 1001 selects a magnification $\alpha C$ and a variance $\sigma C$ which are pieces of statistic information corresponding to region C in the case of subject 1. In the case of subject 2, the CPU 1001 selects a magnification $\alpha B$ and a variance $\sigma B$ which are pieces of statistic information corresponding to region B.

If method 3 (calculation based on the age and breast size of a subject) is selected in step S6003, the CPU 1001 selects, as statistic information to be used subsequently, the values of $\alpha$ and $\sigma$ corresponding to a combination of the age and breast size of the subject acquired in step S6005.

If method 4 (calculation based on the distance between the nipple and the region of interest) is selected in step S6003, the CPU 1001 selects, as statistic information to be used subsequently, the values of $\alpha$ and $\sigma$ corresponding to the distance between the nipple and the region of interest acquired in step S6000.

If method 5 (calculation based on the distance between the body surface and the region of interest) is selected in step S6003, the CPU 1001 derives the body surface and the region of interest, and selects the values of $\alpha$ and $\sigma$ corresponding to the derived distance between the body surface and the region of interest as statistic information to be used subsequently. In this case, the CPU 1001 derives the distance between the body surface and the region of interest by the following processing. First of all, the CPU 1001 functions as the corresponding distance calculation unit 510 to derive a body surface region (a boundary region between the breast region and the outside of the body) by performing image processing for three-dimensional image data. The CPU 1001 then searches for a nearest point at a body surface position with respect to the region of interest, and calculates the distance from the region of interest to the nearest point as the distance between the body surface and the region of interest.

If method 6 (calculation based on the mammary gland density of an object) is selected in step S6003, the CPU 1001 derives the mammary gland density of the object, and selects the values of a and a corresponding to the derived mammary gland density as statistic information to be used subsequently. In this case, the CPU 1001 derives the mammary gland density of the object by the following processing. For example, the CPU 1001 calculates a mammary gland density by acquiring a breast region from three-dimensional image data, classifying a fat region and a mammary gland region in the breast region, and obtaining the proportion of the mammary gland region included in the breast region. The breast region is the region from the body surface to the chest wall, and can be acquired by image processing as a region like a range including the mammary gland outer edges of the left and right breasts in the body side direction. As the above method of classifying the fat region and the mammary gland region in the breast region, for example, there is available a method of classifying them by performing binarization processing for the inside of the breast region with a given threshold. It is possible to obtain the proportion of the mammary gland region in the breast region in this manner and use the resultant value as a mammary gland density. Alternatively, the average value of luminance values in the breast region may be acquired as a value representing a mammary gland density. In addition, a local mammary gland density near a portion between the nipple and the region of interest may be obtained in consideration of the position of a region of interest and the position of the nipple (reference point position). For example, a circular cylinder centered on a line segment connecting the region of interest to the nipple and having a predetermined radius may be defined, and a mammary gland density in the range of the circular cylinder may be obtained. Alternatively, the breast region may be divided into blocks each including approximately several tens of voxels, and a mammary gland density may be obtained in each block. The weighted average of the mammary gland densities in the respective blocks which are weighted in accordance with the distances from the line segment connecting the region of interest to the nipple to the respective blocks may be used as a mammary gland density.

Note that when statistic information is held in the form of a function of input parameters x such as the age of each subject, the breast size, the distance between the nipple and the region of interest, the distance between the body surface and the region of interest, the mammary gland density, and the like, the magnification $\alpha$ and the standard deviation a are calculate by inputting the parameters associated with the subject to the function.

(Step S6030: Image Combining)

In step S6030, the CPU 1001 functions as the image generation unit 540 to generate an image by superimposing information indicating a place where the possibility of the presence of a corresponding region is high on the ultrasonic tomogram based on the ultrasonic tomogram, the position and orientation of the ultrasonic probe, the reference point position, and the corresponding distance. The CPU 1001 then sends the generated image to the display unit 180.

First of all, the image generation unit 540 (CPU 1001) obtains spheres centered on the position of the reference point obtained in step S6020 and respectively having the corresponding distances (r'−2σ, r'−σ, r', r'+σ, and r'+2σ) obtained in step S6025 as radii. In this case, five spheres having the same central position and different radii are obtained.

The image generation unit 540 then obtains a plane in a space containing the ultrasonic tomogram (that is, an ultrasonic slice (imaging slice)) based on the position and orientation of the ultrasonic probe obtained in step S6010, and calculates circles (five circles) obtained by cutting the spheres (five spheres) along the plane. Finally, the image generation unit 540 generates a composite image by superimposing portions (arcs), of the calculated circles, which are included in the ultrasonic tomogram, on the ultrasonic tomogram.

Figure 9:
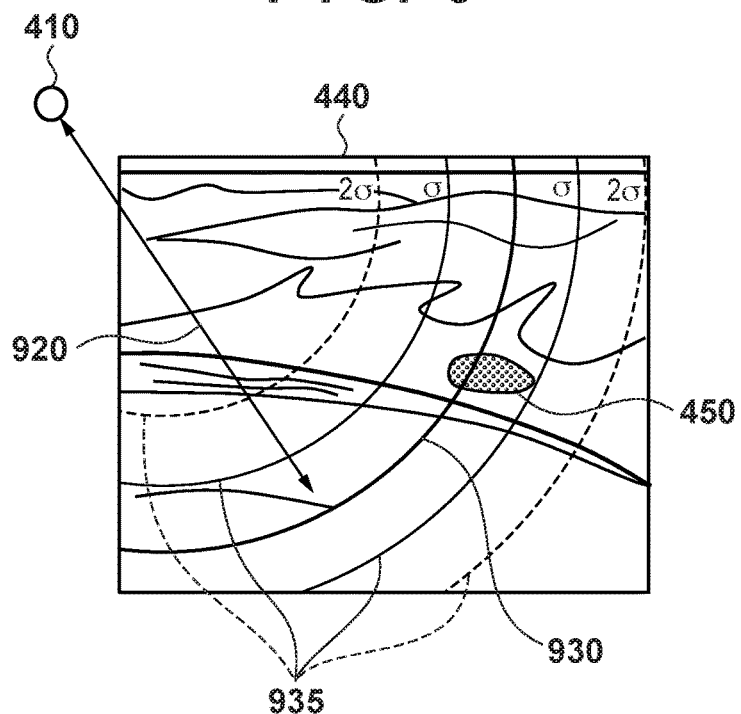
FIG. 9 is a view showing an example of a composite image.
Figure 12B:
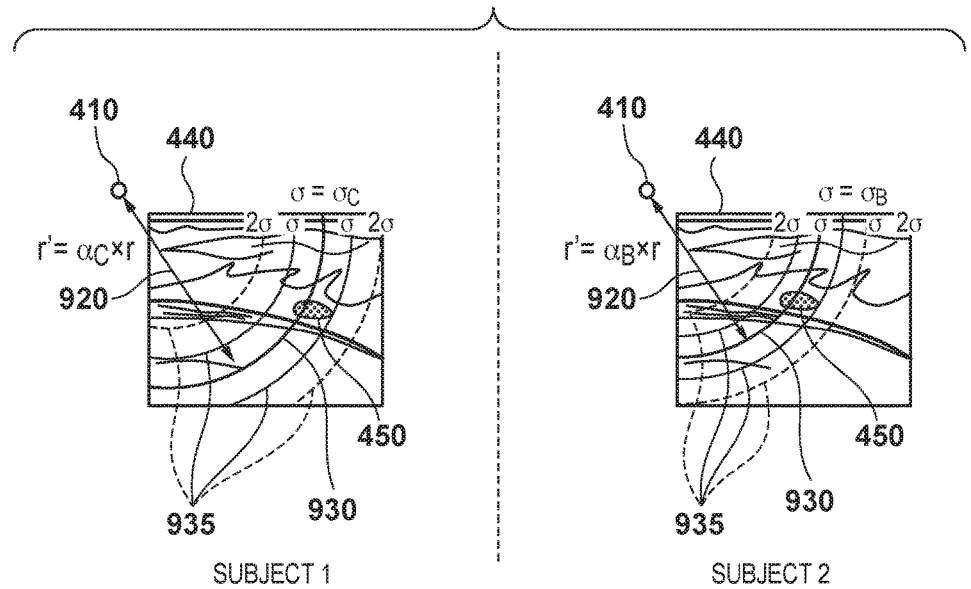

FIG. 9 shows an example of the composite image generated by this processing. Referring to FIG. 9, slices of concentric spheres centered on a nipple position 410 and respectively having corresponding distances as radii are superimposed as an arc 930 and auxiliary lines 935 on an ultrasonic tomogram 440. In addition, pieces of character information ("−2σ", "−σ", "σ", and "2σ") indicating standard deviations are superimposed/displayed as additional information near the respective auxiliary lines. Consider the situation shown in FIG. 12A described above. Even if the distances between the nipples and the regions of interest are the same radius r, information based on statistic information in region C is superimposed/displayed in the case of subject 1, whereas information based on statistic information in region B is superimposed/displayed in the case of subject 2, as shown in FIG. 12B.

Figure 10:
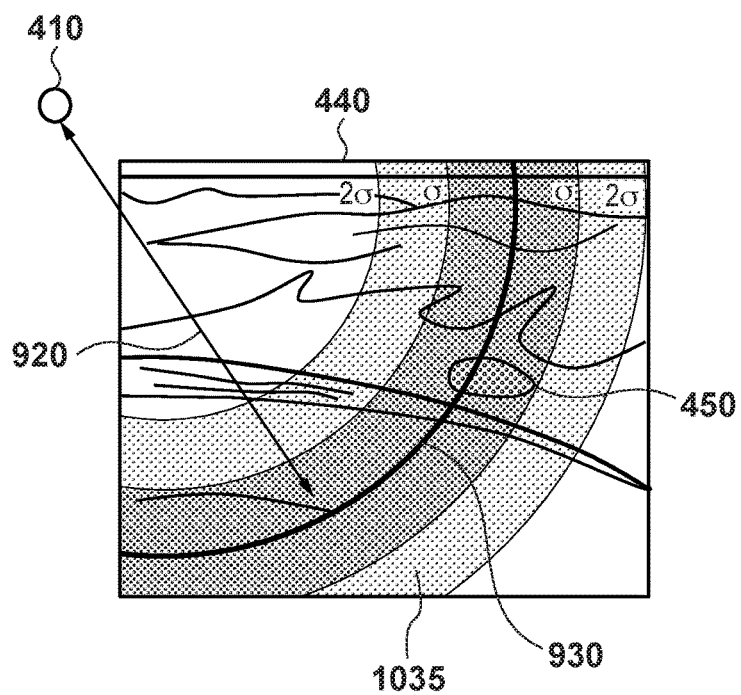
FIG. 10 is a view showing an example of a composite image.

FIG. 10 is another example of the composite image in this embodiment, in which regions falling within the standard deviation σ and regions falling within the standard deviation 2σ are translucently colored to be presented as a presence range 1035. The operator can narrow down the search range by searching for a corresponding region 450 while referring to the support information presented in this manner.

With the above operation, it is possible to draw, in an ultrasonic tomogram, a position at which the possibility of the presence of a corresponding region is high by using statistic information associated with the distance between the nipple and the region of interest, and present the resultant image to the operator. In addition, it is possible to present a position at which the possibility of the presence of a corresponding region is higher by using statistic information corresponding to the attributes of an object or a region of interest. Presenting such a position can present a more effective search range to the operator. This can prevent the operator from making wrong association and further reduce the trouble of searching a wide range.

Third Embodiment

The third embodiment is an embodiment configured to make a presentation in consideration of the spatial spread (size) of a region of interest. An information system according to this embodiment will be described with reference to only differences from the first embodiment. That is, this embodiment is the same as the first embodiment unless specifically mentioned in the following description.

Figure 13:
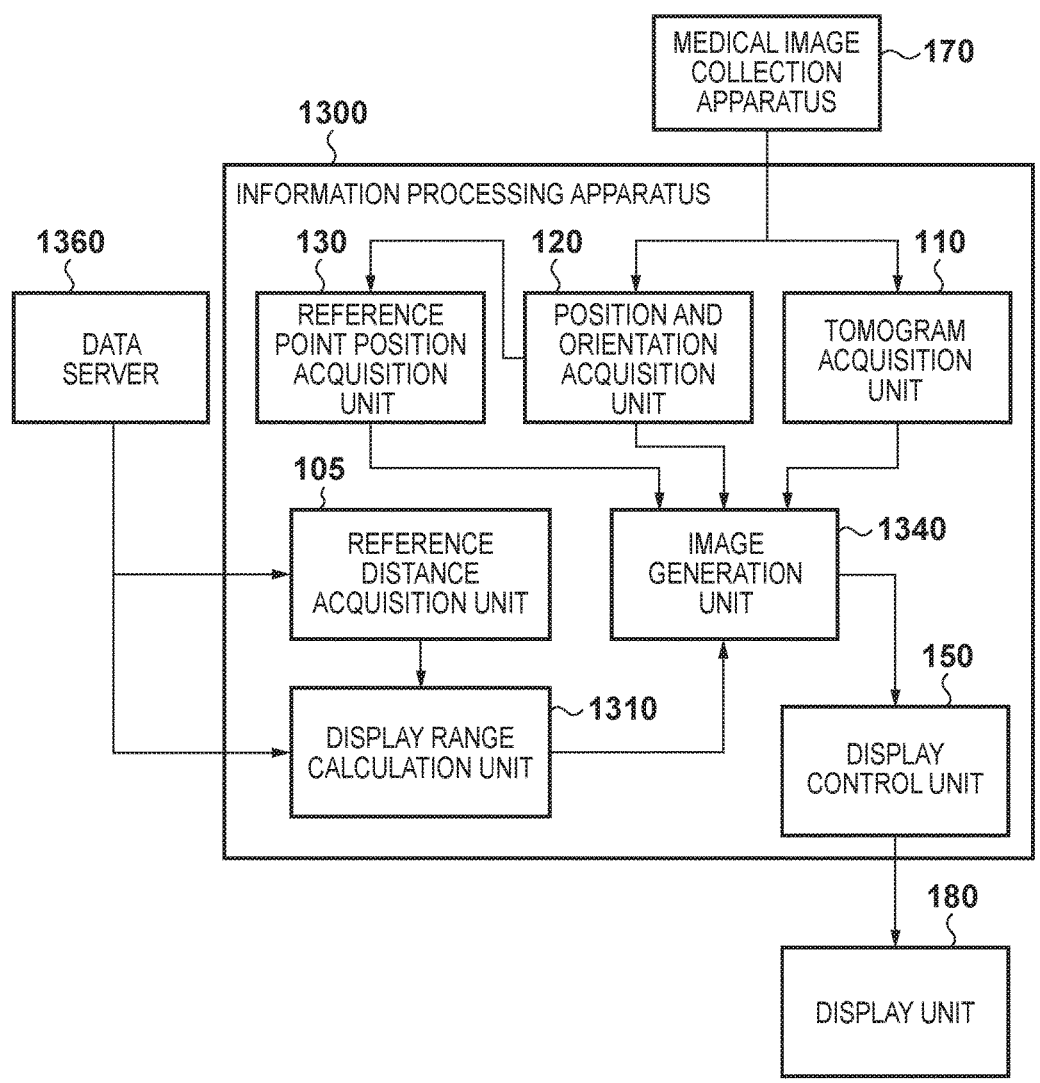
FIG. 13 is a block diagram showing an example of the functional configuration of an information processing system.

The information processing system according to this embodiment will be described with reference to the block diagram of FIG. 13. Note that the same reference numerals as in FIG. 13 denote the same functional units as in FIG. 1, and a description of them will be omitted. As shown in FIG. 13, the information processing system according to the embodiment includes a data server 1360, an information processing apparatus 1300, a medical image collection apparatus 170, and a display unit 180.

The data server 1360 holds information concerning the spatial spread of a region of interest in addition to information such as the distance between the reference point and the region of interest described in the first embodiment. In this case, information concerning the spatial spread of a region of interest is, for example, a maximum diameter R of the region of interest. Alternatively, the information is the distance (minimum distance Dmin) from a reference point to the nearest point of the region of interest and the distance (maximum distance Dmax) to the farthest point. The former information can be obtained by detecting by image processing a region indicating a region of interest from the three-dimensional image data of an object, based on which the distance between the reference point and the region of interest is acquired. The later information can be calculated based on the nipple position in the three-dimensional image data and information labeled to a voxel of the region of interest. The data server 1360 outputs the above held data to the information processing apparatus 1300.

A display range calculation unit 1310 acquires information concerning the spatial spread of a region of interest from the data server 1360. The display range calculation unit 1310 then calculates a display range for a reference distance based on this information. The display range calculation unit 1310 outputs the calculated display range to an image generation unit 1340.

Like the image generation unit 140 in the first embodiment, based on a reference distance, the position of a reference point, and the position and orientation of an ultrasonic probe, the image generation unit 1340 superimposes, on an ultrasonic tomogram, the information of an arc whose distance from the reference point coincides with the reference distance. In addition, the information of a region with a margin with respect to the reference distance is superimposed on the ultrasonic tomogram by further using the value of the display range calculated by the display range calculation unit 1310.

Note that when the respective functional units in the information processing apparatus 1300 shown in FIG. 13 are implemented by computer programs, the computer shown in FIG. 2 can be applied to the information processing apparatus 1300 as in the first embodiment. That is, when the respective functional units in the information processing apparatus 1300 are implemented by computer programs, a CPU 1001 executes the computer programs to make the computer function as the information processing apparatus 1300.

Figure 14:
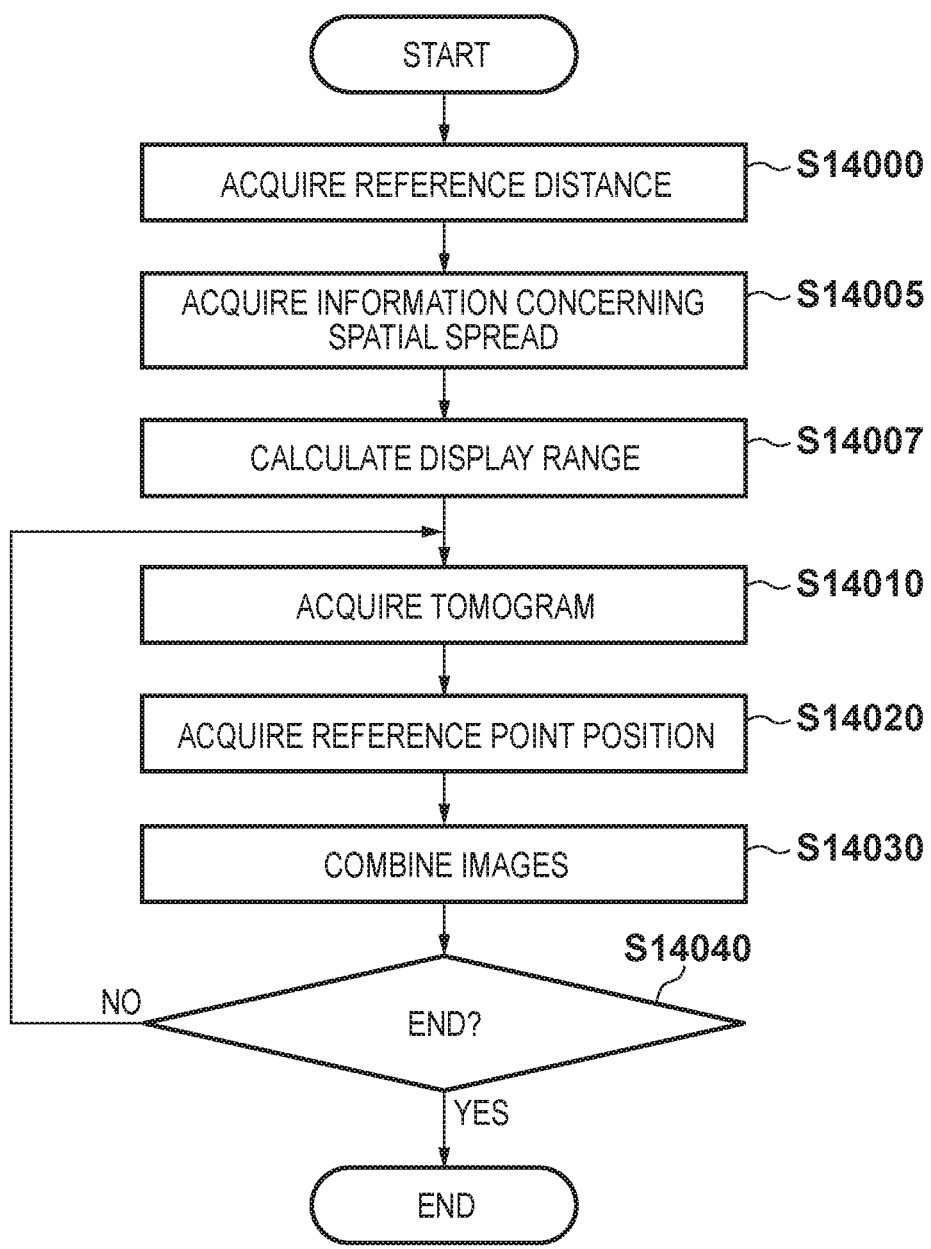
FIG. 14 is a flowchart showing the processing performed by a computer.

The processing performed by the computer in FIG. 2 which operates as the information processing apparatus 1300 will be described next with reference to FIG. 14 showing a flowchart for the processing. Note that an external storage apparatus 1007 stores computer programs and data which make the CPU 1001 execute the processing based on the flowchart of FIG. 14. The CPU 1001 loads the computer programs and data from the external storage apparatus 1007 into a RAM 1002, and executes processing by using the computer programs and data. This makes the computer in FIG. 2 execute the processing based on the flowchart of FIG. 14.

Steps S14000, S14010, S14020, and S14040 in FIG. 14 are the same as steps S3000, S3010, S3020, and S3040 in the flowchart of FIG. 3, and hence a description of these steps will be omitted.

(Step S14005: Acquisition of Spatial Spread of Region of Interest)

In step S14005, the CPU 1001 functions as the display range calculation unit 1310 to acquire information concerning the spatial spread of a region of interest from the data server 1360. For example, the CPU 1001 acquires the maximum diameter R of the region of interest and the minimum distance Dmin and the maximum distance Dmax from the reference point to the region of interest.

(Step S14007: Calculation of Display Range)

In step S14007, the CPU 1001 functions as the display range calculation unit 1310 to calculate a display range based on the information concerning the spatial spread of the region of interest acquired in step S14005. More specifically, the CPU 1001 determines the lower limit value and the upper limit value of the distances from the reference point position as a display range. If, for example, the maximum radius R of the region of interest has been acquired, the range from a lower limit value r−R/2 to an upper limit value r+R/2 is set as a display range based on a reference distance r. Alternatively, if the minimum distance Dmin and the maximum distance Dmax between the nipple and the region of interest have been acquired, the range from the minimum distance Dmin to the maximum distance Dmax is set as a display range.

(Step S14030: Image Combining)

In step S14030, the CPU 1001 functions as the image generation unit 1340 to generate an image by superimposing information indicating a place where the possibility of the presence of a corresponding region is high on the ultrasonic tomogram in consideration of the spatial spread of the corresponding region. More specifically, the CPU 1001 generates a composite image by superimposing, on the ultrasonic tomogram, the display range acquired in step S14007, that is, arcs respectively corresponding to the upper limit value and the lower limit value of distances. Alternatively, the CPU 1001 generates a composite image by superimposing a region enclosed by the arcs on the ultrasonic tomogram upon translucently coloring the region. Note that the processing of obtaining an arc on an ultrasonic tomogram which is located at a predetermined distance from a reference point is the same as the processing for the reference distance in step S3030 in the first embodiment, and hence a description of the processing will be omitted.

FIG. 15 shows an example of a composite image in this embodiment. In this case, an arc 430 at a reference distance is drawn, and at the same time, the range enclosed by spheres centered on the reference point and respectively having radii r−R/2 and r+R/2 is translucently colored and presented as a presence range 1510.

With the above processing, a presentation is made in consideration of the spatial spread of a region of interest. This presentation allows the operator to perform a search in consideration of the spatial spread of the region of interest.

Fourth Embodiment

The pieces of information described as those to be simultaneously displayed on a screen in the above description are not necessarily displayed at once. Some of these pieces of information may be displayed, or they may be switched and displayed in accordance with user instructions.

In addition, according to the above description, a position where the possibility of the presence of a corresponding region is high is drawn in an ultrasonic tomogram in various forms to be presented to the operator. However, such a presentation may lead to misunderstanding depending on the type of lesion, for example, a lesion other than that developed on a mammary gland. For this reason, this embodiment may be configured to switch between performing and not performing the above combining processing depending on the type of lesion.

If, for example, the operator identifies the type of lesion and determines that the lesion is not the one that develops on a mammary gland, he/she may designate not to perform the above combining processing by using a keyboard 1004 or a mouse 1005.

In addition, there is available so-called "Fusion display" to display an ultrasonic tomogram and a corresponding tomogram in the three-dimensional image obtained by MRI on the same screen side by side. In such Fusion display, although images at the same slice position are desired to be displayed side by side, the slice positions of the respective images shift during capturing of ultrasonic tomograms due to the influences of the body motion of a patient and the like.

For this reason, an "alignment mode" and an "imaging mode" are provided. For example, a button image for issuing an instruction to select the "alignment mode" and a button image for issuing an instruction to select the "imaging mode" are displayed on a screen of a display unit 180. When the operator designates the button image of the "alignment mode" by operating the keyboard 1004 or the mouse 1005, a CPU 1001 sets the mode of the computer to the "alignment mode". On the other hand, when the operator designates the button image of the "imaging mode" by operating the keyboard 1004 or the mouse 1005, a CPU 1001 sets the mode of the computer to the "imaging mode". Note that the mode setting method to be used is not limited to this. When the "alignment mode" is set, the CPU 1001 permits the above combining processing. When the "imaging mode" is set, the CPU 1001 inhibits the above combining processing. This makes it possible to present reference information when the operator adjusts the position of the ultrasonic prove so as to display images at the same slice position side by side.

In addition, when performing Fusion display of images in a prone posture and a supine posture, the CPU 1001 may permit the above combining processing, whereas when performing Fusion display of images in supine postures, the CPU 1001 may inhibit the above combining processing.

As described above, it is possible to permit or inhibit the above combining processing in accordance with the purpose or situation of the use of the information processing system. In addition, the CPU 1001 may permit/inhibit combining processing of only arcs and pieces of character information corresponding to the arcs (for example, 5 mm, 10 mm, 15 mm, and the like) instead of inhibiting or permitting the entire combining processing. It is also possible to perform control to display a specific number of sets of arcs and pieces of character information corresponding to the arcs instead of permitting/inhibiting combining processing. For example, the number of display sets is increased in the above "alignment mode", whereas the number of display sets is decreased in the "imaging mode". Alternatively, the operations described above may be combined as needed.

As has been described above, the essence of the above description is based on the technique of acquiring a tomogram of an object, specifying a place in the tomogram which corresponds to a portion spaced apart from a reference point in the object by a predetermined distance, and generating and outputting a composite image having information indicating the specified place on the tomogram.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-188717, filed Sep. 11, 2013, which is hereby incorporated by reference herein in its entirety.

What is claimed is:

1. An information processing apparatus comprising:
one or more processors; and
a memory having stored thereon instructions that, when executed by the one or more processors, cause the information processing apparatus to:
acquire an image of a breast;
acquire information on a position of a nipple of the breast in a three-dimensional coordinate system to which the image of the breast belongs;
specify a plurality of places in the image spaced apart from the nipple of the breast by a plurality of three-dimensional distances set at equal intervals on the basis of the information on the position of the nipple;
generate a composite image including the image and information indicating the plurality of places; and
cause a display unit to display the composite image.

2. The information processing apparatus according to claim 1, wherein the instructions further cause the information processing apparatus to calculate circles by cutting spheres centered on the position of the nipple and having each of the plurality of three-dimensional distances as a radius along an imaging region of the breast which corresponds to the image on the basis of the information on the position of the nipple, and calculate an arc, of each of the calculated circles, which is included in the image.

3. The information processing apparatus according to claim 2, wherein the instructions further cause the information processing apparatus to generate the composite image by superimposing the arc on the image.

4. The information processing apparatus according to claim 1, wherein the instructions further cause the information processing apparatus to generate the composite image by superimposing a character indicating the plurality of three-dimensional distances on the image.

5. The information processing apparatus according to claim 1, wherein, in accordance with a mode designated by a user, the instructions further cause the information processing apparatus to generate and cause the display unit to display the image not included the information indicating the plurality of places or generate and cause the display unit to display the composite image.

6. The information processing apparatus according to claim 1, wherein the instructions further cause the information processing apparatus to acquire the information on the position of the nipple on the basis of a position of the nipple in a physical space which is measured by a position sensor.

7. The information processing apparatus according to claim 1, wherein the instructions further cause the information processing apparatus to:
specify a place in the image spaced apart from the nipple by a reference three-dimensional distance between the nipple and a region of interest in the breast;
generate a further composite image including the image and information indicating the place; and
switch between a first mode for displaying the composite image and a second mode for displaying the further composite image.

8. The information processing apparatus according to claim 1, wherein the image is an ultrasonic tomogram.

9. An information processing method performed by an information processing apparatus, the method comprising:
acquiring an image of a breast;
acquiring information on a position of a nipple of the breast in a three-dimensional coordinate system to which the image of the breast belongs;
specifying a plurality of places in the image spaced apart from the nipple of the breast by a plurality of three-dimensional distances set at equal intervals on the basis of the information on the position of the nipple;
generating a composite image including the image and information indicating the plurality of places; and
causing a display unit to display the composite image.

10. The information processing method according to claim 9, further comprising calculating circles by cutting spheres centered on the position of the nipple and having each of the plurality of three-dimensional distances as a radius along an imaging region of the breast which corresponds to the image on the basis of the information on the position of the nipple, and calculate an arc, of each of the calculated circles, which is included in the image.

11. The information processing method according to claim 10, wherein the composite image is generated by superimposing the arc on the image.

12. The information processing method according to claim 9, wherein the composite image is generated by superimposing a character indicating the plurality of three-dimensional distances on the image.

13. The information processing method according to claim 9, wherein, in accordance with a mode designated by a user, further comprising generating and causing the display unit to display the image not included the information indicating the plurality of places or generating and causing the display unit to display the composite image.

14. The information processing method according to claim 9, wherein the information on the position of the nipple is acquired on the basis of a position of the nipple in a physical space which is measured by a position sensor.

15. The information processing method according to claim 8, further comprising:
specifying a place in the image spaced apart from the nipple by a reference three-dimensional distance between the nipple and a region of interest in the breast;
generating a further composite image including the image and information indicating the place; and
switching between a first mode for displaying the composite image and a second mode for displaying the further composite image.

16. The information processing method according to claim 9, wherein the image is an ultrasonic tomogram.

17. A non-transitory computer-readable storage medium storing a computer program for causing a computer to:
acquire an image of a breast;
acquire information on a position of a nipple of the breast in a three-dimensional coordinate system to which the image of the breast belongs;
specify a plurality of places in the image spaced apart from the nipple of the breast by a plurality of three-dimensional distances set at equal intervals on the basis of the information on the position of the nipple;
generate a composite image including the image and information indicating the plurality of places; and
cause a display unit to display the composite image.

18. An information processing apparatus comprising:
one or more processors; and
a memory having stored thereon instructions that, when executed by the one or more processors, cause the information processing apparatus to:
acquire an image of a breast;
acquire information on a position of a nipple of the breast in a three-dimensional coordinate system to which the image of the breast belongs;
specify a place in the image spaced apart from the nipple of the breast by a three-dimensional distance on the basis of the information on the position of the nipple;
generate a composite image including the image and information indicating the place; and
cause a display unit to display the composite image.

19. The information processing apparatus according to claim 18, wherein the instructions further cause the information processing apparatus to generate the composite image by superimposing a character indicating the three-dimensional distance on the image.

20. The information processing apparatus according to claim 18, wherein, in accordance with a mode designated by a user, the instructions further cause the information processing apparatus to generate and cause the display unit to display the image not included the information indicating the place or generate and cause the display unit to display the composite image.

21. The information processing apparatus according to claim 18, wherein the instructions further cause the information processing apparatus to acquire the information on the position of the nipple on the basis of a position of the nipple in a physical space which is measured by a position sensor.

22. The information processing apparatus according to claim 18, wherein the image is an ultrasonic tomogram.

23. The information processing apparatus according to claim 18, wherein the three-dimensional distance is a three-dimensional distance determined based on a designation of an operator.

24. The information processing apparatus according to claim 18, wherein the three-dimensional distance is a three-dimensional distance between the position of the nipple and a region of interest, which is determined based on an image of the breast different from the image.

25. The information processing apparatus according to claim 18, wherein the three-dimensional distance is a three-dimensional distance between the position of the nipple and a region of interest, which is determined based on a designation of an operator for an image of the breast different from the image.

26. The information processing apparatus according to claim 18, wherein the instructions further cause the information processing apparatus to generate the composite image by superimposing an arc indicating the place on the image.

27. An information processing method performed by an information processing apparatus, the method comprising:
acquiring an image of a breast;
acquiring information on a position of a nipple of the breast in a three-dimensional coordinate system to which the image of the breast belongs;
specifying a place in the image spaced apart from the nipple of the breast by a three-dimensional distance on the basis of the information on the position of the nipple;
generating a composite image including the image and information indicating the place; and causing a display unit to display the composite image.

28. The information processing method according to claim 27, wherein the composite image is generated by superimposing a character indicating the three-dimensional distance on the image.

29. The information processing method according to claim 27, wherein, in accordance with a mode designated by a user, further comprising generating and causing the display unit to display the image not included the information indicating the place or generating and causing the display unit to display the composite image.

30. The information processing method according to claim 27, wherein the information on the position of the nipple is acquired on the basis of a position of the nipple in a physical space which is measured by a position sensor.

31. The information processing method according to claim 27, wherein the image is an ultrasonic tomogram.

32. The information processing method according to claim 27, wherein the three-dimensional distance is a three-dimensional distance determined based on a designation of an operator.

33. The information processing method according to claim 27, wherein the three-dimensional distance is a three-dimensional distance between the position of the nipple and a region of interest, which is determined based on an image of the breast different from the image.

34. The information processing method according to claim 27, wherein the three-dimensional distance is a three-dimensional distance between the position of the nipple and a region of interest, which is determined based on a designation of an operator for an image of the breast different from the image.

35. The information processing method according to claim 27, wherein the composite image is generated by superimposing an arc indicating the place on the image.

* * * * *